(12) United States Patent
Sun et al.

(10) Patent No.: US 11,867,634 B2
(45) Date of Patent: Jan. 9, 2024

(54) DUAL-SENSOR DETECTION OF REFLECTANCE SIGNALS FOR THIN-FILM BASED ASSAYS

(71) Applicant: Ortho-Clinical Diagnostics, Inc., Raritan, NJ (US)

(72) Inventors: Qi Sun, Raritan, NJ (US); Jian Zheng, Raritan, NJ (US); Stephen Daggett, Raritan, NJ (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 592 days.

(21) Appl. No.: 17/127,027

(22) Filed: Dec. 18, 2020

(65) Prior Publication Data

US 2021/0190696 A1 Jun. 24, 2021

Related U.S. Application Data

(60) Provisional application No. 62/950,833, filed on Dec. 19, 2019.

(51) Int. Cl.
| | |
|---|---|
| *G01N 21/77* | (2006.01) |
| *G01N 33/72* | (2006.01) |
| *G02B 5/08* | (2006.01) |
| *H04N 23/56* | (2023.01) |

(52) U.S. Cl.
CPC .......... *G01N 21/77* (2013.01); *G01N 33/726* (2013.01); *G01N 33/728* (2013.01); *G02B 5/0833* (2013.01); *H04N 23/56* (2023.01)

(58) Field of Classification Search
CPC .... G01N 21/77; G01N 33/726; G01N 33/728; G01N 33/54391; G01N 2021/7773; G02B 5/0833; H04N 23/56
USPC ........ 356/369; 252/408.1; 436/12, 164, 166, 436/169, 177, 178, 527, 531, 534, 8, 97
See application file for complete search history.

(56) References Cited

U.S. PATENT DOCUMENTS

| | | | | |
|---|---|---|---|---|
| 5,652,148 A | * | 7/1997 | Doshi ................ | G01N 33/5002 210/729 |
| 2010/0189600 A1 | * | 7/2010 | Hulteen ............... | G01N 21/783 422/420 |

\* cited by examiner

*Primary Examiner* — Eric S. McCall
*Assistant Examiner* — Timothy P Graves
(74) *Attorney, Agent, or Firm* — K&L Gates LLP; Louis C. Cullman; Dennis A. Majewski

(57) ABSTRACT

The present disclosure is directed to a thin-film element that enables analytes to be analyzed on separate surfaces. In an example, a thin-film element includes a first layer for processing a fluid sample to generate a first analyte and a second analyte. The thin-film element also includes a second layer configured to be impermeable to the first analyte to enable the first analyte to be retained by the first layer and permeable to the second analyte to enable the second analyte to pass through the second layer. The thin-film element further includes a third layer configured to retain the second analyte. The second layer includes a first reflective surface and a second reflective surface to provide reflectance signals indicative of analytes present in the first and third layers to sensors located on opposite sides of the thin-film element.

17 Claims, 3 Drawing Sheets

DUAL-SENSOR DETECTION OF REFLECTANCE SIGNALS FOR THIN-FILM BASED ASSAYS

PRIORITY CLAIM

This application claims priority to and the benefit of U.S. Provisional Patent Application Ser. No. 62/950,833, filed on Dec. 19, 2019, the entire disclosure of which is hereby incorporated by reference.

TECHNICAL FIELD

The present disclosure relates generally to a thin-film element and corresponding device for analyzing a fluid sample, and more specifically to a device for measuring reflectance signals from both sides of a thin-film element.

BACKGROUND

Conventional thin-film based assays are performed by measuring reflectance signals from one surface of a thin-film element using a single sensor. In some cases, the single sensor may sequentially analyze multiple analytes from the same surface of the thin-film element. However, when multiple analytes are analyzed from the same surface, it is possible that one analyte can interfere with another. For example, in the case of an HbA1c assay, methemoglobin (the analyte for hemoglobin) can complicate the measurement of Fructosyl valine-histidine (fVH) (the analyte for HbA1c).

SUMMARY

The present disclosure is directed to a thin-film element that enables analytes to be analyzed on separate surfaces, and to a corresponding device that is configured to measure reflectance signals from the separate surfaces of the thin-film element to perform the analysis. In a general example embodiment, a device for analyzing a fluid sample includes a thin-film element comprising a first layer for processing the fluid sample to generate a first component and a second component. The thin-film element also includes a second layer configured to be impermeable to the first component to allow the first component to be retained by the first layer and permeable to the second component to allow the second component to pass through the second layer. The second layer includes a first reflective surface and a second reflective surface. The thin-film element further includes a third layer configured to retain the second component. The device additionally includes a first sensor positioned towards the first layer. The first reflective surface of the second layer is configured to generate a first optical signal by reflecting a first light modulated by the first component, where the first sensor is configured to receive the first optical signal. The device further includes a second sensor positioned towards the third layer, where the second reflective surface of the second layer is configured to generate a second optical signal by reflecting a second light modulated by the second component. The second sensor is configured to receive the second optical signal.

In another embodiment, the device includes a first light source positioned towards the first layer, where light from the first light source is modulated by the first component to generate the first optical signal. The device also includes a second light source positioned towards the third layer, where light from the second light source is modulated by the second component to generate the second optical signal.

In another embodiment, the device includes a first optical filter configured to filter the first optical signal before the first optical signal is received by the first sensor, and a second optical filter configured to filter the second optical signal before the second optical signal is received by the second sensor. In some embodiments, the optical filter can be located between a light source and a thin film element. In other embodiments, the optical filter can be located between a thin film element and an optical sensor. In still other embodiments, an optical filter can be located both between a light source and a thin film element and between a thin film element and an optical sensor.

In another embodiment, the first sensor comprises at least one of a photo multiplier tube, a contact-image sensor, a photodiode, and an image capturing sensor matrix, and the second sensor comprises at least one of a photo multiplier tube, a contact-image sensor, a photodiode, and an image capturing sensor matrix.

In another embodiment, the second layer comprises a gelatin and an optical masking material that provides the first reflective surface and the second reflective surface of the second layer.

In another embodiment, the optical masking material comprises $TiO_2$.

In another embodiment, the first sensor generates a first electrical signal in response to the first optical signal and the second sensor generates a second electrical signal in response to the second optical signal. The device further includes a processor in communication with the first sensor and the second sensor to receive the first electrical signal and the second electrical signal. The processor is configured to determine or generate a ratio between the first component and the second component based on the first electrical signal and the second electrical signal.

In some embodiments, the sample comprises multiple components, for example, a first component and a second component. A first and second component are provided for illustration purposes only, three or more components may also be included in a sample. In some embodiments, the different components can include some property difference, such as but not limited to, molecular weight, size, molecular complexity, charge, van der Waals forces, hydrophobicity, hydrophilicity, and the like. In one embodiment, the difference can be molecular weight. In such an embodiment, the components can be calcium and albumin, which have very different molecular weights. The first layer can include at least one reagent for processing the fluid sample to generate the first component and the second component. In some embodiments, the at least one reagent is a compound that can generate or separate components based on a property difference.

In another embodiment, the sample comprises a human or animal blood sample, the first layer includes at least one reagent for processing the fluid sample to generate the first component and the second component, the at least one reagent comprising a lysing agent, a denaturing agent, and a protease for processing the blood sample to provide Hb and a peptide derived from HbA1c, where the first component of the blood sample comprises the Hb and the second component of the blood sample comprises the peptide (e.g., glycopeptide) derived from HbA1c.

In another embodiment, the third layer comprises at least one reagent configured to process the second component to generate a third component of the sample, and the second light is modulated by the third component.

In another embodiment, the thin-film element is moveable between the first sensor and the second sensor in a direction substantially perpendicular to a direction defined from the first sensor to the second sensor, such that a plurality of the first optical signals are generated by the first reflective surface and received by the first sensor and a plurality of the second optical signals are generated by the second reflective surface and received by the second sensor upon the movement of the thin-film slide.

In another embodiment, the first layer is a top layer, the second layer is a middle layer, the third layer is a bottom layer, the first sensor is a top sensor, and the second sensor is a bottom sensor.

In a general example embodiment, a method of analyzing a fluid sample includes moving a thin-film element between a first sensor and a second sensor in a direction substantially perpendicular to a vertical direction defined from the first sensor to the second sensor. The thin-film element comprises a first layer for processing the fluid sample to generate a first component and a second component, and a second layer configured to be impermeable to the first component to allow the first component to be retained by the first layer and permeable to the second component to allow the second component to pass through the second layer, where the second layer comprises a first reflective surface and a second reflective surface. The thin-film element also includes a third layer configured to retain the second component. The method also includes simultaneously generating a first optical signal by reflecting a first light modulated by the first component off of the first reflective surface and generating a second optical signal by reflecting a second light modulated by the second component off of the second reflective surface, and simultaneously receiving the first optical signal by the first sensor and receiving the second optical signal by the second sensor.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein, and it is expressly contemplated to claim individual advantageous embodiments separately. Moreover, it should be noted that the language used in the specification has been selected principally for readability and instructional purposes, and not to limit the scope of the inventive subject matter.

BRIEF DESCRIPTION OF THE DRAWINGS

Embodiments of the present disclosure will now be explained in further detail by way of example only with reference to the accompanying figures, in which.

DETAILED DESCRIPTION

The present disclosure relates to methods and apparatuses for analyzing a fluid sample, for example a human or animal sample, on a thin-film element. Fluid samples can be blood or a blood component or other liquids. Fluids can include, but are not limited to blood, urine, saliva, cerebral spinal fluid, bile, sweat, seminal fluid, plasma, serum, vaginal fluid, tears, vitreous fluid, or the like. In one embodiment, the fluid sample is a human or animal blood sample.

Figure 1:
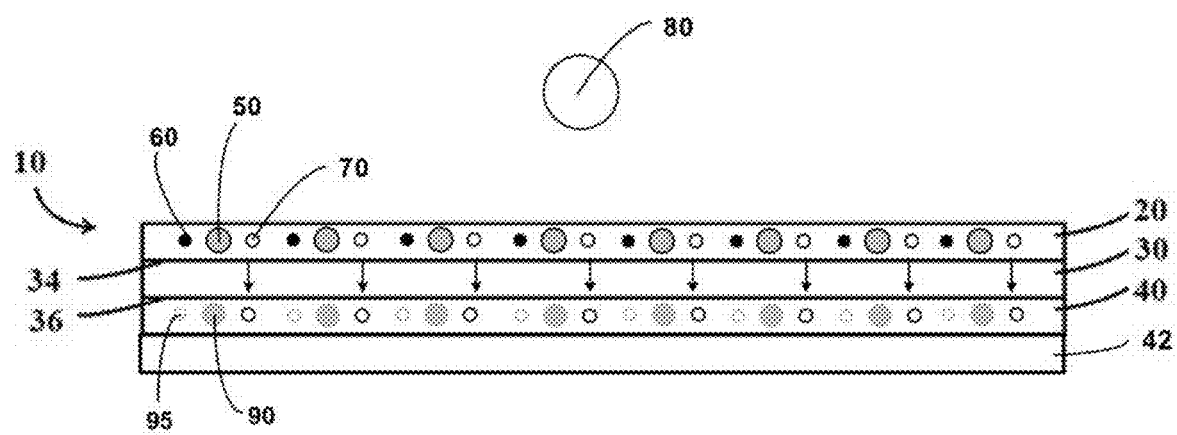
FIG. 1 is a side view of an example embodiment of a thin-film element. according to the present disclosure.
Figure 2:
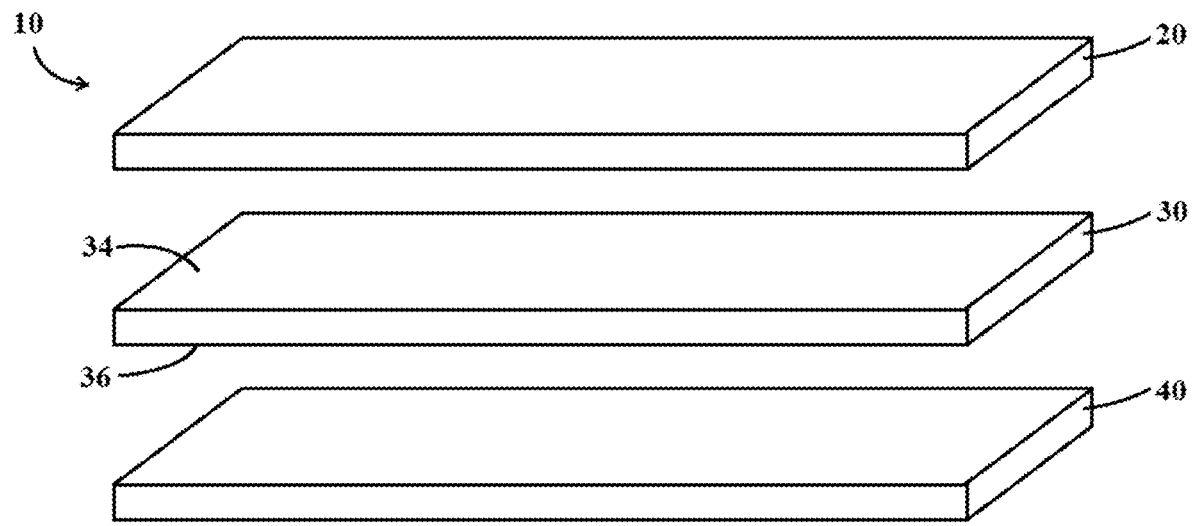
FIG. 2 is an exploded perspective view of the thin-film element of FIG. 1.
Figure 3:
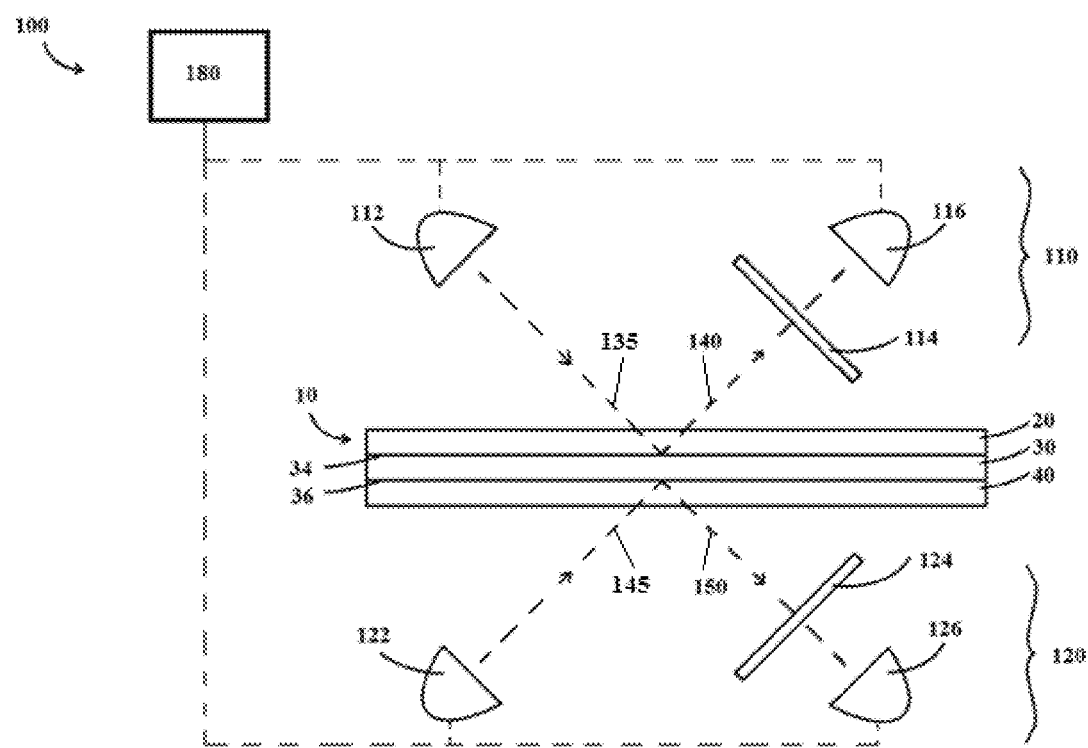
FIG. 3 is a side view of an example embodiment of a device and thin-film element. according to the present disclosure.

FIGS. 1 and 2 illustrate an example embodiment of a thin-film element 10, according to the present disclosure. FIG. 3 illustrates an example embodiment of an analysis device 100 according to the present disclosure which is configured to analyze a fluid sample dispensed on the thin-film element 10 shown in FIGS. 1 and 2.

As illustrated in FIGS. 1 and 2, the thin-film element 10 includes a plurality of layers. In the illustrated embodiment, the thin-film element 10 includes a first or top layer 20, a second or middle layer 30, and a third or bottom layer 40. Those of ordinary skill in the art will recognize that additional layers can be added to the thin-film element 10, or the existing layers can be divided into additional layers, without changing the function of thin-film element 10 as described herein.

In some embodiments, the thin-film element 10 can be formed on a support layer 42. Support layer 42 can be a transparent material such as, but not limited to polyester or other transparent plastic material. In some embodiments, this support material can remain on the element during use.

First layer 20 of the thin-film element 10 is configured to initially receive a fluid sample 80 for analysis. Fluid sample 80 may be a blood sample including serum, plasma, or whole blood. In an embodiment, first layer 20 may include one or more reagent 50 that processes fluid sample 80 to produce analytes, such that the one or more reagent 50 generates a first component 60 and a second component 70 from the fluid sample when the fluid sample is placed on the first layer 20. In an embodiment, first layer 20 may be transparent or partially opaque so as to not affect reflectance of an optical signal modulated by the fluid sample 80, as explained in more detail below. In some embodiments, the composition of the first layer may be 30 µm polymeric beads supported by a water soluble polymer.

In an example embodiment, the one or more reagent 50 can include a lysing agent, a denaturing agent, and/or a protease for processing the fluid sample, for example, to generate hemoglobin (Hb) and a peptide derived from HbA1c. In this example, the first component 60 of the blood sample may include the Hb and the second component 70 of the blood sample may include the peptide derived from HbA1c. The one or more reagent 50 in first layer 20 may lyse the red blood cells, denature the hemoglobin, and release fVH (HbA1c analyte) from the hemoglobin molecules as a result of proteolysis. As described in further detail below, the denatured hemoglobin molecules may then be retained in first layer 20 due to the composition of second layer 30. Denatured modified methemoglobin has characteristically strong light absorption at ~540 nm, which enables detection by a sensor detecting light reflecting from first layer 20.

In an embodiment, the one or more reagent 50 can include a glucose oxidant such as glucose oxidase.

Second layer 30 of thin-film element 10 is configured to be impermeable to the first component 60 (e.g., Hb) of the fluid sample, and permeable to the second component 70 (e.g., the peptide derived from HbA1c) of the fluid sample. In this manner, the second layer 30 enables the second component 70 to pass therethrough to third layer 40, while the first component is retained in first layer 20. In an embodiment, the permeability/impermeability through second layer 30 may be based on molecule size and/or molecular weight. In other embodiments, the permeability/impermeability through second layer 30 may be based on ion exchange, ion transport, barrier layers, and the like.

Second layer 30 may include at least one reflective surface so that the first component 60 retained by first layer 20 may be analyzed separately from the second component 70 retained by third layer 40, and vice versa, as explained in more detail below. For example, the at least one reflective surface may include a first or top reflective surface 34 and a second or bottom reflective surface 36, which enable the first component 60 and the second component 70 to be analyzed from opposite sides of the thin-film element 10. In an embodiment, second layer 30 may be formed of a gelatin, and may include an optical masking material such as $TiO_2$ that creates the at least one reflective surface including top reflective surface 34 and/or the bottom reflective surface 36.

In other embodiments, the second layer can be formed of $BaSO_4$. This barium layer can include a reflective material such as $TiO_2$ that creates the at least one reflective surface.

Third layer 40 of thin-film element 10 is configured to retain the second component 70 (e.g., the peptide derived from HbA1c) of the fluid sample once it has passed from first layer 20 through second layer 30. In an embodiment, third layer 40 may be transparent, partially opaque so as not to affect reflectance of an optical signal modulated by the second component 70, as explained in more detail below. In some embodiments, the third layer 40 can be formed of a material such as, but not limited to, gelatin, synthetic polymers, and the like.

Third layer 40 may include one or more second reagents 90 configured to process the second component 70 to generate a third component 95. The second reagents 90 can be the same or different than the first reagent. In one embodiment, they are different. In an embodiment, third layer 40 may include one or more second reagent 90 that processes the second component 70 into a chromogen, e.g., third component 95, once the second component 70 is received by third layer 40. For example, with the HbA1c example, where the second component 70 includes fVH, the one or more second reagent 90 in third layer 40 can process the fVH (e.g., Oxidase→$H_2O_2$→HRP→Blue Leuco Dye cascade), where the result can be detected by a sensor measuring reflectance.

In other embodiments, many different analytes can be detected with an appropriate reagent. In some embodiments, bound/free analytes can be used. Analytes can include, but are not limited to glucose, blood urea nitrogen (BUN), creatinine, sodium, lithium, calcium, magnesium, unconjugated bilirubin, conjugated bilirubin, unconjugated delta bilirubin, and the like.

In some embodiments, a reagent may not be required.

As illustrated in FIG. 3, the device 100 is configured to accept the thin-film element 10 and analyze the thin-film element 10 from opposite sides. In the illustrated embodiment, the device 100 includes a first or upper assembly 110 and a second or lower assembly 120. First assembly 110 may include a first light source 112, a first optical filter 114 and a first sensor 116 configured to be used to analyze the first component 60 retained by first layer 20 of the thin-film element 10. The lower assembly 120 may include a second light source 122, a second optical filter 124, and a second sensor 126 configured to be used to analyze the second component 70 retained by third layer 40 of the thin-film element 10. FIG. 3 illustrates that first light source 112 illuminates at 45 degrees and first sensor 116 reads at 45 degrees (total oriented at 90 degrees relative to one another).

In other words, the light beam reflects and is detected at 90 degrees. A similar configuration is illustrated for second light source 122 and second sensor 126. However, in some embodiments, to avoid specular reflections, the light source can illuminate at 45 degrees and the sensor can read the signal at 90 degrees relative to the sample.

Though FIG. 3 shows the thin-film element 10 as set within the device 100, it should be understood that the thin-film element 10 is moveable between first assembly 110 and second assembly 120, for example, in a direction substantial perpendicular to a vertical direction defined from first assembly 110 to second assembly 120. When positioned as shown in FIG. 3, a plurality of first optical signals 140 may be generated when a first light 135 from first light source 112 reflects off of first reflective surface 34 and is modulated by first component 60, while a plurality of second optical signals 150 may be generated when a second light 145 from second light source 122 reflects off of second reflective surface 36 and is modulated by second component 70.

In the illustrated embodiment, first light source 112 is provided above first layer 20 and is configured to project a first light 135 onto first layer 20 so that the first light 135 may be modulated by the first component 60 of the fluid sample retained by first layer 20. First light source 112 may include, for example, one or more light-emitting diode ("LED") lights or another type of lighting structure understood to those of ordinary skill in the art. Those of ordinary skill in the art will recognize that other configurations for first light source 112 are possible, for example, by placing thin-film element 10 in a non-horizontal configuration with first light source 110 to the side, or by placing first light source 112 in another location and using a reflector above first layer 20 to guide first light 135 towards first layer 20.

In the illustrated embodiment, second light source 122 is provided below third layer 40 and is configured to project a second light 145 onto third layer 40 so that the second light 145 may be modulated by the second component 70 of the fluid sample retained by third layer 40. Second light source 122 may include, for example, one or more LED lights or another type of lighting structure understood to those of ordinary skill in the art. Those of ordinary skill in the art will recognize that other configurations for second light source 122 are possible, for example, by placing thin-film element 10 in a non-horizontal configuration with second light source 122 to the side, or by placing second light source 122 in another location and using a reflector below third layer 40 to guide second light 145 towards third layer 40.

In an alternative embodiment, a single light source can be used in place of first light source 112 and second light source 122. For example, the single light source could project light towards both sides of thin-film element 10, with reflectors being used to direct the first light 135 towards first layer 20 and the second light 145 towards third layer 40.

In the illustrated embodiment, first optical filter 114 is provided above first layer 20 and configured to filter a first optical signal 140 generated by the first light 135 being modulated by first component 60 and reflected off of first reflective surface 34, before the first optical signal 140 is received by first sensor 116. In an embodiment, first optical filter 114 may be a band pass filter of an appropriate wavelength for the assay being run. Those of ordinary skill in the art will recognize that other configurations for first optical filter 114 are possible, for example, by placing the thin-film element 10 in a non-horizontal configuration with first optical filter 114 to the side. Other types of optical filters can include, but are not limited to absorptive filters and dichroic filters. In some embodiments, a diffraction grating or a monochromater can also be used to select a particular wavelength of light.

In the illustrated embodiment, second optical filter 124 is provided below third layer 40 and configured to filter a second optical signal 150 generated by the second light 145 being modulated by second component 70 and reflected off of second reflective surface 36, before the second optical signal 150 is received by second sensor 126. In an embodiment, second optical filter 124 may be a band pass filter of an appropriate wavelength for the assay being run. Those of ordinary skill in the art will recognize that other configurations for second optical filter 124 are possible, for example, by placing the thin-film element 10 in a non-horizontal configuration with second optical filter 124 to the side.

In the illustrated embodiment, first sensor 116 is provided above first layer 20 and is configured to receive the first optical signal 140 after the first optical signal 140 has been generated by the first light 135 being modulated by first component 60 and reflected off of first reflective surface 34, and after the first optical signal 140 passes through first optical filter 114. In an embodiment, first sensor 116 may include at least one of a photo multiplier tube, a contact-image sensor, a photodiode, and an image capturing sensor matrix. Those of ordinary skill in the art will recognize that other configurations for first sensor 116 are possible, for example, by placing thin-film element 10 in a non-horizontal configuration with first sensor 116 to the side.

In the illustrated embodiment, second sensor 126 is provided beneath third layer 40 and is configured to receive the second optical signal 150 after the second optical signal 150 has been generated by the second light 145 being modulated by second component 70 and reflected off of second reflective surface 36, and after the second optical signal 150 passes through second optical filter 124. In an embodiment, second sensor 126 may include at least one of a photo multiplier tube, a contact-image sensor, a photodiode, and an image capturing sensor matrix. Those of ordinary skill in the art will recognize that other configurations for second sensor 126 are possible, for example, by placing thin-film element 10 in a non-horizontal configuration with second sensor 126 to the side.

The device 100 may further include or be placed in communication with a processor 180, which may control the elements of first assembly 110 and second assembly 120 individually or as a whole, sending signals to first assembly 110 and second assembly 120 and receiving signals therefrom. In an embodiment, processor 180 may receive a first electrical signal generated by first sensor 116 in response to first sensor 116 sensing the first optical signal 140, and may receive a second electrical signal generated by second sensor 126 in response to second sensor 126 sensing the second optical signal 150. The first electrical signal and the second electrical signal may indicate, for example, measured intensities of the first optical signal 140 and second optical signal 150, respectively.

In some embodiments, multiple measurements can be made over time to calculate a rate of reaction. In some embodiments, these multiple measurements over time can include at least an early blank reading and then a final reading. A response can be calculated by subtracting the early blank from the final reading.

Processor 180 may then process the signals, for example, by generating a ratio between the concentration of first component 60 and the concentration of second component 70 of the fluid sample based on the first electrical signal and the second electrical signal. In some embodiments, image processing can be used to obtain a result if the sensor is included in or part of an imaging reflectometer.

In other embodiments, processor 180 may then process the signals, for example, by calculating concentrations of two different analytes or sample components based on the first electrical signal and the second electrical signal.

Other types of algorithms can be used for calculation. Other algorithms can include, but are not limited to, a product of two measurements divided by a constant to yield a risk score or measuring the amount of interferent for the analyte of choice and an algorithm that eliminates bias.

Figure 4:
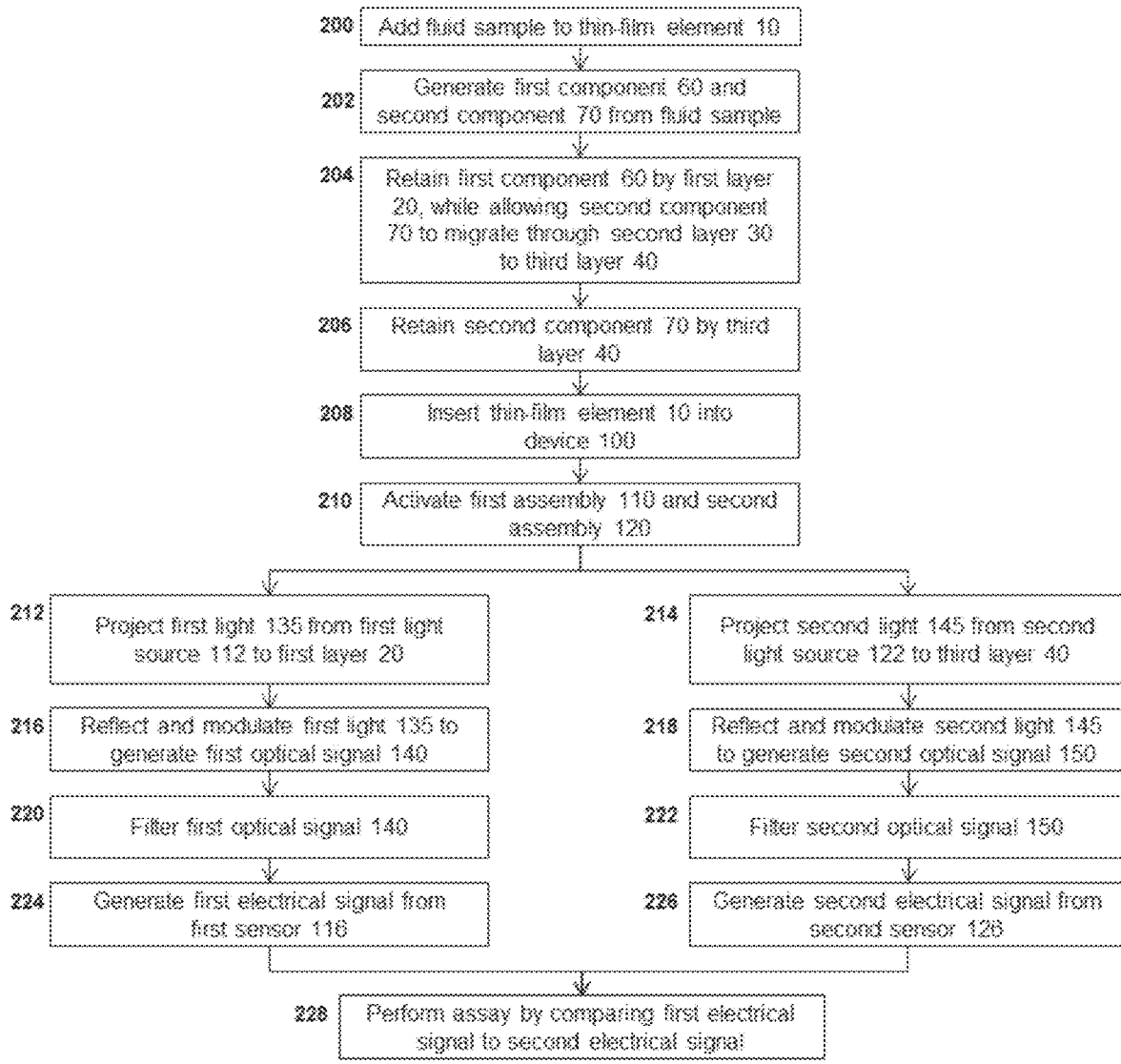
FIG. 4 is a flow chart showing an example embodiment of a method of using the device and thin-film element of the present disclosure.

FIG. 4 illustrates a method of performing an assay using the thin-film element 10 with the device 100 of FIGS. 1 to 3, according to an example embodiment of the present disclosure. Those of ordinary skill in the art will recognize that certain steps may be omitted from or added to those shown in FIG. 4 without departing from the spirit and scope of the present disclosure.

At step 200, a fluid sample is dispensed on first layer 20 of thin-film element 10. The fluid sample may be, for example, a human or animal blood sample including serum, plasma, or whole blood. The fluid sample may be added to first layer 20 before thin-film element 10 is inserted into device 100, or the fluid sample may be added with thin-film element 10 already positioned between first assembly 110 and second assembly 120 of device 100.

At step 202, the fluid sample dispensed on first layer 20 of thin-film element 10 reacts with the one or more reagent 50 of first layer 20 to create the first component 60 and the second component 70. The reaction may take place before or after thin-film element 10 is inserted into device 100 and/or positioned between first assembly 110 and second assembly 120 of device 100.

In other embodiments, a first component and a second component may already exist in the fluid sample and no reaction to produce them may be required. In one embodiment, a first component may be glucose and the second component may be albumin, both in a blood sample not requiring a reaction.

At step 204, first component 60 is retained by first layer 20 because second layer 30 is impermeable to first component 60, while second component 70 migrates through second layer 30 to third layer 40 because second layer 30 is permeable to second component 70. As with step 202, the migration of second component 70 through second layer 30 to third layer 40 may take place before or after thin-film element 10 is inserted into device 100 and/or positioned between first assembly 110 and second assembly 120 of device 100.

At step 206, second component 70 is retained by third layer 40. In an embodiment, third layer 40 may include one or more reagent 80 to react with second component 70 once second component 70 migrates through second layer 30. For example, the one or more reagent 80 may generate a third component from second component 70 that will act to modulate second optical signal 150. As with steps 202 and 204, step 206 may take place before or after thin-film element 10 is inserted into device 100 and/or positioned between first assembly 110 and second assembly 120 of device 100.

At step 208, if thin-film element 10 is not already positioned between first assembly 110 and second assembly 120 of device 100, thin-film element 10 may be manually or automatically positioned between first assembly 110 and second assembly 120 of device 100. In an embodiment, thin-film element 10 is moveable between first assembly 110 and second assembly 120 in a direction substantial perpendicular to a vertical direction defined from first assembly 110 to second assembly 120. Those of ordinary skill in the art will understand that different insertions directions and/or configurations are possible.

At step 210, processor 180 initiates an analysis procedure by activating first assembly 110 and second assembly 120. In FIG. 4, processor 180 is shown to control first assembly 110 and second assembly 120 simultaneously and independently, though those of ordinary skill in the art will recognize that first assembly 110 and second assembly 120 can also be controlled sequentially or together with a single control structure that activates both assemblies using a single signal.

At step 212, processor 180 causes first light source 112 to project the first light 135 towards first layer 20, while at step 214, processor 180 causes second light source 122 to project the second light 145 towards third layer 40. The first light 135 and second light 145 may be, for example, light signals generated by one or more LED's. In the embodiment illustrated in FIG. 3, the first light 135 and second light 145 are projected at an angle of 45° to facilitate accurate measurements, but those of ordinary skill in the art will recognize that other configurations may be possible as describe herein.

In other embodiments, fluorescence and/or luminescence can be used.

At step 216, the first optical signal 140 is generated as the first light 135 reflects off of second layer 30 and is modulated by the first component 60 retained by the first layer 20, while at step 218, the second optical signal 150 is generated as the second light 145 reflects off of second layer 30 and is modulated by the second component 70 retained by third layer 40. In an embodiment, the first optical signal 140 is reflected by the first reflecting surface 34 of second layer 30, while the second optical signal 150 is reflected by the second reflecting surface 36 of second layer 30. It should further be understood that modulation by the first component 60 includes modulation by additional components generated from the first component, and modulation by the second component includes modulation by additional components generated from the second component. For example, as explained above, one or more reagent 80 contained by third layer 40 may generate a third component from the second component, which then modulates the second optical signal 150.

At step 220, the first optical signal 140 is filtered by first optical filter 114, while at step 222, the second optical signal 150 is filtered by the second optical filter 124. As will be understood by those of ordinary skill in the art, the first optical filter 114 and the second optical filter 124 should each have an appropriate wavelength for the assay being run. In an embodiment, the first optical filter 114 and the second optical filter 124 may be automatically adjusted by processor 180 to an appropriate wavelength, or manually adjusted by a user based on the assay being run.

At step 224, first sensor 116 generates a first electrical signal in response to first sensor 116 sensing the first optical signal 140 after passing through first optical filter 114, while at step 226, second sensor 126 generates a second electrical signal in response to second sensor 126 sensing the second optical signal 150 after passing through second optical filter 124. In the embodiment illustrated in FIG. 3, the first optical signal 140 and second optical signal 150 are received by first sensor 116 and second sensor 126 at an angle of 45° to facilitate accurate measurements, but those of ordinary skill in the art will recognize that other configurations may be possible. The first electrical signal and the second electrical signal are then relayed to processor 180 for further processing. The first electrical signal and the second electrical signal may indicate, for example, measured intensities of the respective first optical signal 140 and second optical signal 150, which may indicate respective concentrations of the first component 60 and second component 70.

In some embodiments, other types of optical outputs can be utilized. These can include, but are not limited to surface plasmon resonance (SPR) diffraction by ring resonators, output by a waveguide, output by an interferometer, or output by a photonic detector.

At step 228, processor 180 receives the first electrical signal from first sensor 116 and the second electrical signal from second sensor 126 and performs an analysis using the two signals. In an embodiment, the analysis includes a comparison of a concentration of the first component 60 based on the first electrical signal and a concentration of the second component 70 based on the second electrical signal, for example, by calculating a ratio between the concentrations and making a determination based on the numerical value of the ratio.

It is contemplated that an advantageous use of thin-film element 10 and/or device 100 could be in the performance of an HbA1c assay, where methemoglobin, which is the analyte for hemoglobin, complicates the measurement of Fructosyl valine-histidine (fVH), the analyte for HbA1c. The use of separate layers (e.g., first layer 20 and third layer 40) for measurement of each analyte, has several advantages, for example, reduced assay time, increased reliability, and reduced cost.

In the example of an HbA1c assay, a fluid sample (e.g. whole blood) can be dispensed on first layer 20. The one or more reagent contained by first layer 20 may then lyse the red blood cells, denature hemoglobin, and release fVH (HbA1c analyte) from the hemoglobin molecules as a result of proteolysis. The denatured hemoglobin molecules (e.g., the first component) are retained by first layer 20 due to the gelatin in the second layer 30. In this case, detergent modified methemoglobin has characteristically strong light absorption at about 540 nm, which allows detection by first sensor 116 by measuring reflectance. The first electrical signal generated by the first sensor 112 can therefore indicate the concentration of hemoglobin (Hb) in the blood sample.

Fructosyl valine-histidine (fVH) (e.g., the second component) is small enough that it can pass through the gelatin in the second layer, so it passes through second layer 30 to third layer 40 where it is retained. At third layer 40, the fVH can be processed (e.g., Oxidase→$H_2O_2$→HRP→Blue Leuco Dye cascade), where the result can be detected by second sensor 126 by measuring reflectance at about 670 nm. The second electrical signal generated by the second sensor 126 can then indicate the concentration of HbA1c in the blood sample.

Once the processor 180 receives the first electrical signal and the second electrical signal, the processor may determine the result of the assay by calculating the ratio of HbA1c:Hb. Determination of the ratio of HbA1c:Hb in this way is advantageous over systems that measure both concentrations on the same side of a thin-film element, for example, because it is possible for one analyte to interfere with the other.

In other embodiments, a slide without reagents can be used. Therein, components of the sample such as but not limited to unconjugated/conjugated bilirubin can be used to transport a component that can modulate an optical signal. Unconjugated bilirubin is typically bound to albumin. In some embodiments, this unconjugated bilirubin can be retained in the top layer because the albumin is impermeable to the second layer. In contrast, conjugated bilirubin can make its way through the second layer into the third layer because it is not bound to albumin. Then, direct measurements by reflectance can be performed and the processor can provide a result.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the disclosure and does not pose a limitation on the scope of the disclosure otherwise claimed. No language in the specification should be construed as indicating any non-claimed element essential to the practice of the disclosure.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of the disclosure are described herein, including the best mode known to the inventors for carrying out the disclosure. Of course, variations on those preferred embodiments will become apparent to those of ordinary skill in the art upon reading the foregoing description. The inventor expects those of ordinary skill in the art to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

Further, it is to be understood that the embodiments of the disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

The invention is claimed as follows:

1. A device for analyzing a fluid sample, the device comprising:
   a thin-film element comprising:
      a first layer for processing the fluid sample to generate a first component and a second component,
      a second layer configured to be impermeable to the first component to allow the first component to be retained by the first layer and permeable to the second component to allow the second component to pass through the second layer, wherein the second layer includes a first reflective surface and a second reflective surface, and
      a third layer configured to retain the second component;
   a first sensor positioned towards the first layer, wherein the first reflective surface of the second layer is configured to provide a first optical signal by reflecting a first light modulated by the first component, wherein the first sensor is configured to receive the first optical signal; and
   a second sensor positioned towards the third layer, wherein the second reflective surface of the second layer is configured to provide a second optical signal by reflecting a second light modulated by the second component, wherein the second sensor is configured to receive the second optical signal.

2. The device of claim 1, further comprising:
   a first light source positioned towards the first layer, wherein light from the first light source is modulated by the first component to generate the first optical signal; and a second light source positioned towards the third layer, wherein light from the second light source is modulated by the second component to generate the second optical signal.

3. The device of claim 1, further comprising:
a first optical filter configured to filter the first optical signal before the first optical signal is received by the first sensor; and
a second optical filter configured to filter the second optical signal before the second optical signal is received by the second sensor.

4. The device of claim 1,
wherein the first sensor comprises at least one of a photo multiplier tube, a contact-image sensor, a photodiode, and an image capturing sensor matrix; and
wherein the second sensor comprises at least one of a photo multiplier tube, a contact-image sensor, a photodiode, and an image capturing sensor matrix.

5. The device of claim 1, wherein the second layer comprises:
a gelatin; and
an optical masking material that provides the first reflective surface and the second reflective surface of the second layer.

6. The device of claim 5, wherein the optical masking material comprises $TiO_2$.

7. The device of claim 1, wherein the first sensor generates a first electrical signal in response to the first optical signal and the second sensor generates a second electrical signal in response to the second optical signal.

8. The device of claim 7, further comprising a processor in communication with the first sensor and the second sensor to receive the first electrical signal and the second electrical signal,
wherein the processor is configured to determine a ratio between the first component and the second component based on the first electrical signal and the second electrical signal.

9. The device of claim 1,
wherein the sample comprises a human or animal sample;
wherein the first layer includes at least one reagent for processing the fluid sample to generate the first component and the second component, the at least one reagent comprising a lysing agent, a denaturing agent, and a protease for processing the blood sample to provide Hb and a peptide derived from HbA1c; and
wherein the first component of the blood sample comprises the Hb and the second component of the blood sample comprises the peptide derived from HbA1c.

10. The device of claim 1,
wherein the third layer comprises at least one reagent configured to process the second component to generate a third component of the sample; and
wherein the second light is modulated by the third component.

11. The device of claim 1, wherein the thin-film element is moveable between the first sensor and the second sensor in a direction substantially perpendicular to a direction defined from the first sensor to the second sensor, such that a plurality of the first optical signals are provided by the first reflective surface and received by the first sensor and a plurality of the second optical signals are provided by the second reflective surface and received by the second sensor upon the movement of the thin-film slide.

12. The device of claim 1, wherein the first layer is a top layer, the second layer is a middle layer, the third layer is a bottom layer, the first sensor is a top sensor, and the second sensor is a bottom sensor when the device is positioned for operation.

13. The device of claim 1, wherein the first component includes a first analyte and the second component includes a second analyte.

14. A method of analyzing a fluid sample, the method comprising:
moving a thin-film element between a first sensor and a second sensor in a direction substantially perpendicular to a vertical direction defined from the first sensor to the second sensor, wherein the thin-film element comprises:
a first layer for processing the fluid sample to generate a first component and a second component,
a second layer configured to be impermeable to the first component to allow the first component to be retained by the first layer and permeable to the second component to allow the second component to pass through the second layer, wherein the second layer comprises a first reflective surface and a second reflective surface, and
a third layer configured to retain the second component;
simultaneously generating a first optical signal by reflecting a first light modulated by the first component off of the first reflective surface and generating a second optical signal by reflecting a second light modulated by the second component off of the second reflective surface; and
simultaneously receiving the first optical signal by the first sensor and receiving the second optical signal by the second sensor.

15. A device for analyzing a fluid sample, the device comprising:
a thin-film element comprising:
a first layer for processing the fluid sample including a first component and a second component,
a second layer configured to be impermeable to the first component to allow the first component to be retained by the first layer and permeable to the second component to allow the second component to pass through the second layer, wherein the second layer includes a first reflective surface and a second reflective surface, and
a third layer configured to retain the second component;
a first sensor positioned towards the first layer, wherein the first reflective surface of the second layer is configured to generate a first optical signal by reflecting a first light modulated by the first component, wherein the first sensor is configured to receive the first optical signal; and
a second sensor positioned towards the third layer, wherein the second reflective surface of the second layer is configured to generate a second optical signal by reflecting a second light modulated by the second component, wherein the second sensor is configured to receive the second optical signal.

16. The device of claim 15, wherein the first component is delta bilirubin.

17. The device of claim 15, wherein the second component is conjugated bilirubin.

* * * * *